US00PP13612P2

(12) United States Plant Patent
Vardi et al.

(10) Patent No.: US PP13,612 P2
(45) Date of Patent: Mar. 4, 2003

(54) CITRUS TREE NAMED 'KEDEM'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,479

(22) Filed: Nov. 20, 2000

(51) Int. Cl.[7] ..... A01H 5/00
(52) U.S. Cl. ..... Plt./202
(58) Field of Search ..... Plt./202

*Primary Examiner*—Kent L. Bell
(74) *Attorney, Agent, or Firm*—Akerman Senterfitt

(57) ABSTRACT

A new variety of mandarin citrus is described that is distinguished by very early fruit ripening and by the orange-red color of the fruit exterior skin.

2 Drawing Sheets

FIELD OF THE INVENTION

A new mandarin citrus *Citrus reticulata* hybrid is described. The new variety designated 'KEDEM' is desirable to the consumer because of its attractive orange-red color and to the commercial grower because of the early maturing of its fruit.

BACKGROUND OF THE NEW PLANT

The present invention relates to a new and distinct variety of mandarin *Citrus reticulata* hybrid developed by inventors Aliza Vardi, Pinchas Spiegel-Roy, Avraham Elchanati, Ahuva Frydman-Shani and Hana Neumann in Bet Dagan, Israel from a selection of plants grown from irradiated buds of the cultivar 'Rishon'.

Asexual reproduction by recognized grafting techniques of the new variety in Israel has shown that the new characteristics are stabilized and permanently fixed through successive propagation.

The objective in breeding the present new variety, known by the designate 'KEDEM' was to induce seedless varieties through mutation breeding in easy peeling varieties. In the spring of 1989, about 100 buds of an easy peeling mandarin cultivar, 'Rishon' (U.S. Plant Pat. No. 8,377), were irradiated at the Weizmann Institute of Science, Rehovat, Israel, by exposure to 3.5 kh of gamma radiation from a Co60 source (G.B. 150A, Atomic Energy of Canada). 'Rishon' was the result of a controlled pollination cross, made at the Volcani Center, Bet Dagan, Israel, in 1978 between 'Temple' (Citrus temple Hort. ex Y. Tanaka) as a pollen parent and 'Michal' (unpatented) as a pollen parent. 'Michal' is a cultivar of Israeli origin believed to be a natural hybrid between two *Citrus reticulata* 'Blanco' cultivars.

Troyer nucellar rootstocks were bud grafted with the individual buds of irradiated 'Rishon' bud wood and labeled $mV_1$. Six to nine months after grafting the irradiated budwood, individual buds from the $mV_1$ plants were re-grafted on Troyer nucellar rootstocks to establish about 300 $mV_2$ plants.

Field planting was established from container grown $mV_2$ plants in the spring of 1991. The first fruits were observed in October 1995 and a second observation made in October 1997.

A selection designated 13/5/82 had medium size orange color fruit, was easy to peel and had few seeds. The selection was distinguished from 'Rishon' as having 0–5 seeds per fruit as compared with 5–11 seeds for 'Rishon' and having a lower pollen fertility of 72% compared with 95% for 'Rishon' when pollen grains were stained with acetocarmine.

SUMMARY OF THE INVENTION

The selection, designated 'KEDEM', is a new variety of mandarin citrus that has a fruit with few seeds and flowers having anthers bearing pollen with low fertility compared to the parent 'Rishon'. Table 1 shows some of the characteristics of 'KEDEM' compared to the parent 'Rishon'.

TABLE 1

| Plant | Fruit color[1] | Chromosome number | Seeds/fruit | Pollen fertility[2] |
|---|---|---|---|---|
| 'KEDEM' | Orange RHS 25A | 2n = 18 | 0–5 | 72% |
| 'Rishon' | Green-yellow | 2n = 18 | 5–11 | 95% |

[1]Observed early in season, October in Bet Dagan, Israel
[2]Estimated by acetocarmine staining observed early in season, October in Bet Dagan, Israel The tree shape is similar to that of 'Rishon'. The tree is vigorous and has small thorns in the leafy part of branches, especially in the lower portion and on the lower part of fruit bearing branches. Main branches have an upright attitude and young shoots have no anthocyanin coloration at the tip.

The fruits of selection 'KEDEM' develop the exterior orange color very early in the season, beginning in October, while at the same time the exterior color of the fruits of 'Rishon' are green-yellow. The bearing of the tree is regular and the productivity is good, about the same as for 'Rishon'. The canopy is moderately dense. The bark of the young shoots is initially smooth and green gradually turning into a smooth yellow-green.

The chromosome number of 'KEDEM' is diploid (2n=18) as is the chromosome number of 'Rishon'.

The leaves of 'KEDEM' are similar to those of 'Rishon'. They are lanceolate and sharp pointed, small to medium in size. Leaf blade is firm, without undulation and straight concave in cross section. Petioles are without wings or have rudimentary wings.

The characteristics of the flowering and the flower parts are similar to those of 'Rishon'. Flowering for both occurs at the end of March or during the first half of April as measured in Bet Dagan, Israel. Both 'KEDEM' and 'Rishon' produce about the same number of flowers and flower drop for both occurs in April. Terminal flower buds have no anthocyanin coloration. Flowers are borne singly and have an average number of stamens (about 20) with complete style development. Anther color is yellow. About 72.5% of the pollen grains were stained with acetocarmine in a test conducted at the Agricultural Research Organization, the Volcani Center, as compared with about 95% staining for 'Rishon' pollen grain.

The fruit has few seeds, about 0–5, even when optimal pollination conditions are employed. This compares with about 5–9 seeds per fruit in 'Rishon'. Except for color development, the fruit characteristics of 'KEDEM' are in the range of the parent cv. 'Rishon'.

The fruit shape is oblate and small to medium sized. When 50 fruits were measured, the fruit had an average weight 79 grams, an average height of 51 mm, and an average diameter of 56.5 mm. The fruit occasionally has a short necked and a depressed distal end. The fruit surface is usually smooth with an orange color, RHS 25A on The Royal Horticultural Society of London Colour Chart, and bears an average number of conspicuous rind oil glands. Fruit ripening does not differ from outside of the canopy to the inside, but the fruit color of the outside canopy is a little brighter compared to the fruit color of the inside canopy. There is no persistence of the style and the areola is not completely developed. A navel is absent or very rare. The rind is thin and easy to peel.

The color of the albedo is white and the flesh is yellow-orange in color. The fruit contains 9–11 segments and is very juicy. The seeds are small, smooth and polyembryonic as are the seeds of the parent 'Rishon'. The external color of the seeds is ivory when fresh and yellowish when dry. The internal seed coat is white and the cotyledons are greenish. Polyembryonic seeds are present. The seed size, shape and texture are similar to that of the parent 'Rishon'. The fruit reaches maturity early or very early in the season as does 'Rishon', which in Israel is late September to October. The ripening of the fruit on the tree and within the fruit is uniform. Fruit remaining on the tree does not regreen. If there is a heavy crop and the fruits are not picked the following season, the tree may produce less fruit (becomes alternate bearing). Pre-harvest drop of both developed and undeveloped fruit is similar to that of the parent cv. 'Rishon'.

The results of the test conducted Oct. 15, 1997 on juice of representative ripe fruit of the new variety were as follows:

Total soluble solids (TSS): 14.9%.
*Acid content.*—1.02%.
*TSS/acid ratio.*—14.55.

DESCRIPTION OF THE PHOTOGRAPHS

The photographs show the whole tree and canopy shape (Sheet 1) as well as the exterior of the new fruit (Sheet 2) illustrating the exterior of 'KEDEM' as well as transversal midsection in a plane substantially perpendicular to the axis.

DESCRIPTION OF THE NEW TREE

The following is a detailed description of the new mandarin citrus variety 'KEDEM' based on observations made under typical Israeli grove conditions. Observations were made on trees approximately 4–6 years old. Color designations are designated as determined from The Royal Horticultural Colour Chart published by The Royal Horticultural Society.

Tree:
- *Origin.*—Irradiation of cv. 'Rishon'.
- *Classification.*—Botanical: *Citrus reticulata* hybrid. Common: Mandarin citrus. Cultivar: 'KEDEM'.
- *Shape.*—Upright, moderately spreading.
- *Thorns.*—1–3 mm length (leafy part of branches particularly on lower part of fruit bearing branches).
- *Branching.*—Upright.
- *Canopy.*—Moderately dense.
- *Bark.*—Immature: Smooth and green, RHS 137B. Mature: Smooth and yellow-green, RHS 146A.
- *Habit.*—Moderately vigorous.
- *Leaf.*—Lanceolate, sharp pointed, color of typical leaf: Green RHS 147A (upper), Green RHS 147B (lower). Size: Small to medium: 83 mm length, 42 mm width. Leaf blade: Firm, without undulation and straight concave in cross section. Petioles: Wingless or rudimentary wings and 9 mm in length, 2 mm in diameter, Green RHS 147B.
- *Height.*—2.5–3 m (8 years old).
- *Disease resistance.*—No particular susceptibility or resistance observed.
- *Trunk diameter.*—7 cm at 20 cm above the ground.
- *Winter hardiness.*—Winter temperature in Bet Dagan, Israel averages 4–7 degrees Centigrade.

Flower:
- *Flowering period.*—Late March to early April in Bet Dagan, Israel.
- *Flower drop.*—April.
- *Stamens.*—Approximately 20.
- *Anther color.*—Yellow-orange RHS 20A.
- *Pollen fertility.*—72.5% staining with acetocarmine.
- *Anthocyanin coloration.*—*None.*

Fruit:
- *Shape.*—Oblate.
- *Size.*—Small to medium.
- *Weight.*—79 g (average of 50 fruits).
- *Height.*—51 mm.
- *Diameter.*—56.5 mm.
- *Skin color.*—Orange RHS 25A.
- *Rind oil gland.*—Average.
- *Style.*—No persistence.
- *Navel.*—Absent.
- *Rind.*—Thin and easy to peel.
- *Albedo.*—White.
- *Flesh color.*—Yellow-orange.
- *Fruit segments.*—9–11.
- *Time to maturity.*—End of September to end of October in Israel under moderate climatic conditions.
- *Fruit extract.*—(Test conducted Oct. 15, 1997 on juice of representative fruit). Total soluble solids (TSS) 14.9%. Acid content: 1.02%. TSS/acid ratio 14.55. Flavor: Pleasant.

Seeds:
- *Color.*—External: Yellow-green, RHS 149D. Internal: Grey-brown, RHS 199C.
- *Cotyledons.*—Green RHS 142C.

*Embryony.*—Polyembryonic (more than one embryo per seed).

The tree and fruit described herein may vary in slight detail due to climate and/or soil conditions under which the variety is grown.

What is claimed is:

1. A new and distinct variety of *Citrus reticulata* hybrid tree substantially as herein described and shown.

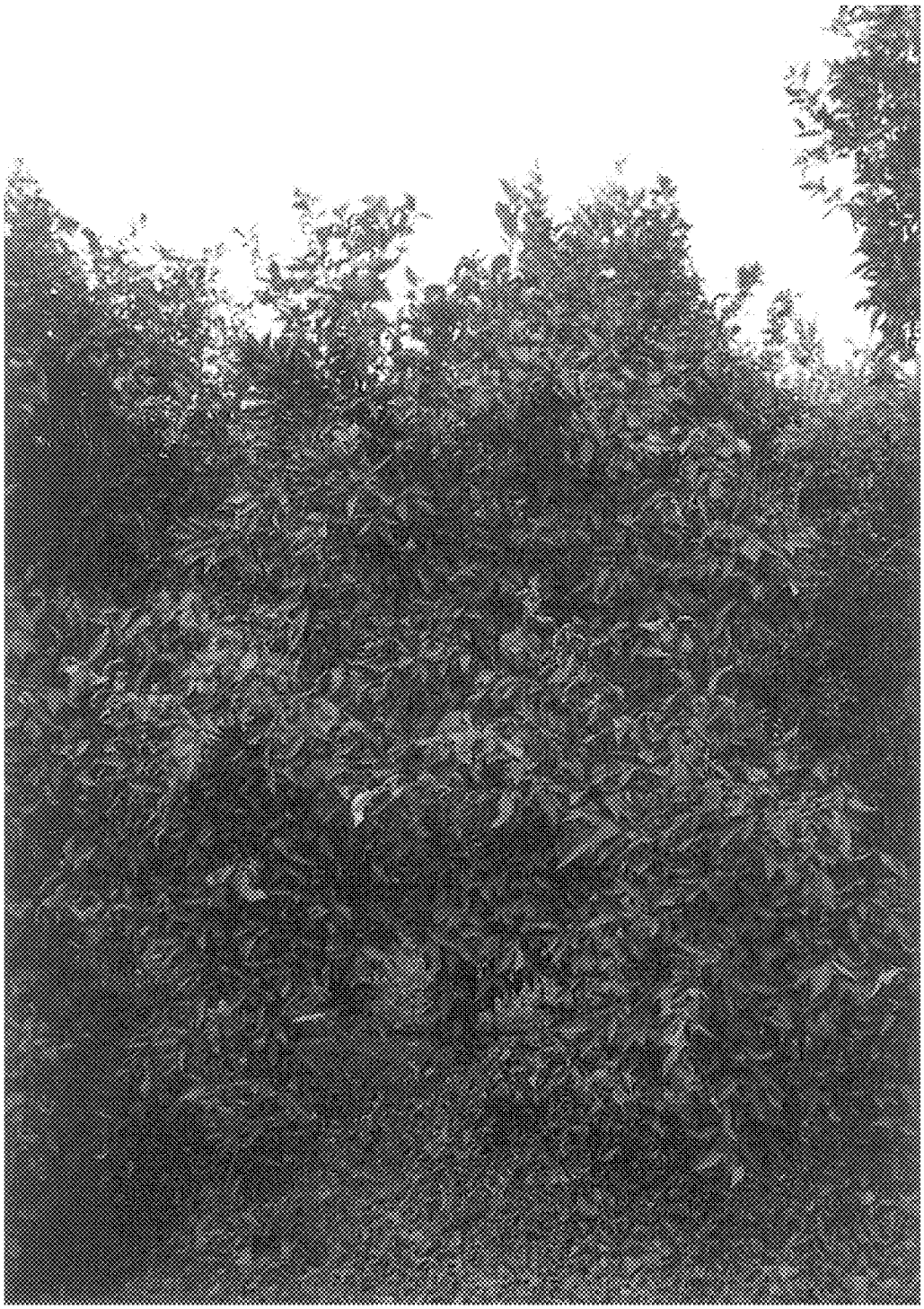

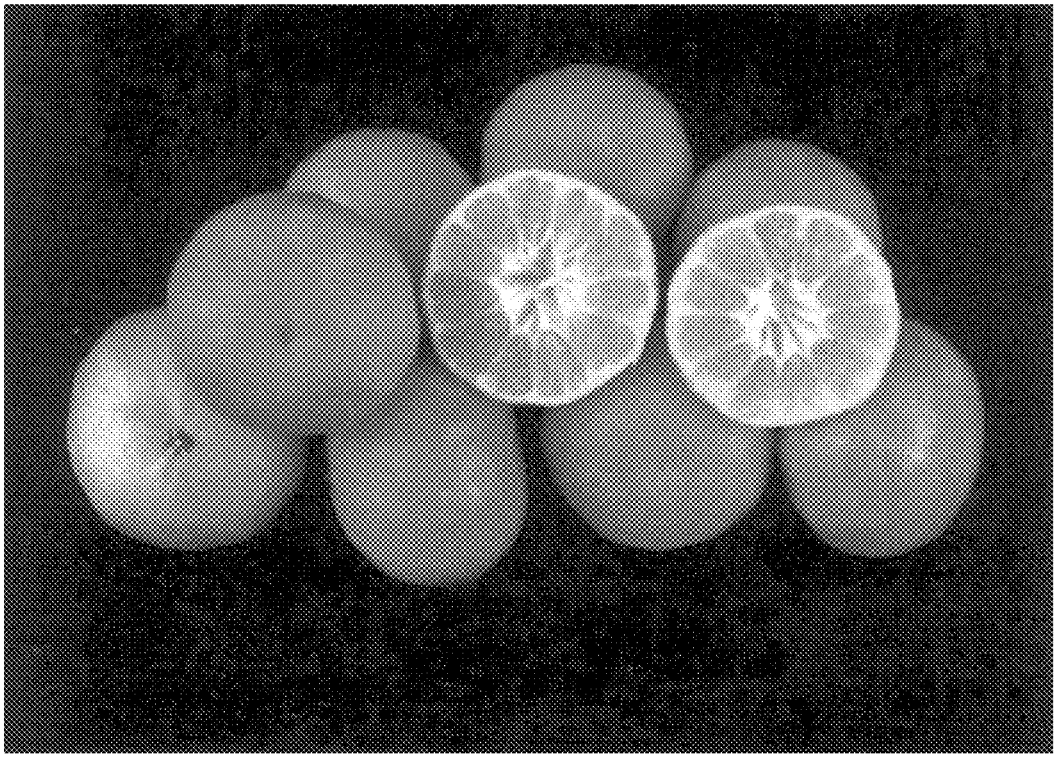

* * * * *